(12) United States Patent
Armstrong et al.

(10) Patent No.: US 11,694,852 B2
(45) Date of Patent: Jul. 4, 2023

(54) ELECTRODES

(71) Applicant: OXFORD UNIVERSITY INNOVATION LIMITED, Oxford (GB)

(72) Inventors: Fraser Armstrong, Oxford (GB); Clare Megarity, Oxford (GB); Thomas Roberts, Oxford (GB); Bhavin Siritanaratkul, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 449 days.

(21) Appl. No.: 16/085,798

(22) PCT Filed: Mar. 20, 2017

(86) PCT No.: PCT/GB2017/050771
§ 371 (c)(1),
(2) Date: Sep. 17, 2018

(87) PCT Pub. No.: WO2017/158389
PCT Pub. Date: Sep. 21, 2017

(65) Prior Publication Data
US 2020/0135411 A1    Apr. 30, 2020

(30) Foreign Application Priority Data
Mar. 18, 2016 (GB) .................................... 1604671

(51) Int. Cl.
*H01G 9/20*    (2006.01)
*G01N 33/53*   (2006.01)
(Continued)

(52) U.S. Cl.
CPC .............. *H01G 9/2027* (2013.01); *C12P 1/00* (2013.01); *C12Q 1/005* (2013.01); *G01N 33/53* (2013.01); *G01N 2333/90293* (2013.01)

(58) Field of Classification Search
CPC ............ H01G 9/20–9/2095; C12P 1/00; C12P 1/001–1/006
See application file for complete search history.

(56) References Cited

U.S. PATENT DOCUMENTS

| 5,885,657 | A  |   | 3/1999  | Penth |
|-----------|----|---|---------|-------|
| 2007/0196659 | A1 | * | 8/2007 | Setoyama ........... H01M 4/9083 428/408 |
| 2010/0282601 | A1 | * | 11/2010 | Nomura ................ H01G 9/205 204/242 |

FOREIGN PATENT DOCUMENTS

| GB | 2486303  | 6/2012 |
|----|----------|--------|
| JP | S5513072 | 1/1980 |

(Continued)

OTHER PUBLICATIONS

Nadtochenko et al ("Nanophotobiocatalysts Based on Mesoporous Titanium Dioxide Films Conjugated with Enzymes and Photosynthetic Reaction Centers of Bacteria", High Energy Chemistry, vol. 42, No. 7, 2008, pp. 591-593). (Year: 2008).*

(Continued)

*Primary Examiner* — Alexander W Keeling
(74) *Attorney, Agent, or Firm* — Barnes & Thornburg LLP

(57) ABSTRACT

An electrode (1), the electrode (1) comprises a substrate (4, 5) on which is located a porous layer of a conducting or semi-conducting oxide (6) and having located thereon Ferredoxin NADP Reductase (FNR) (3). The electrode (1) can be used to drive organic synthesis via nicotinamide cofactor regeneration.

19 Claims, 11 Drawing Sheets

(51) Int. Cl.
    C12P 1/00    (2006.01)
    C12Q 1/00    (2006.01)

(56) References Cited

FOREIGN PATENT DOCUMENTS

| RU | 2416644 | 4/2011 |
|---|---|---|
| WO | WO2016/007204 | 1/2016 |

OTHER PUBLICATIONS

Cosnier et al ("A glucose biosensor based on enzyme entrapment within polypyrrole films electrodeposited on mesoporous titanium dioxide", Journal of the Electroanalytical Chemistry, 469, 1999, pp. 176-181). (Year: 1999).*

Liu et al ("Macroporous indium tin oxide electrode layers as conducting substrates for immobilization of bulky electroactive guests", Electrochemica Acta, 140, 2014, pp. 108-115). (Year: 2014).*

Horiba ("What is a nanoparticle?"). (Year: 2008).*

Topoglidis et al ("Factors that Affect Protein Adsorption on Nanostructured Titania Films. A Novel Spectroelectrochemical Application to Sensing", Langmuir, 2001, 17, 7899-7906) (Year: 2001).*

Madoz et al ("Investigation of the diaphorase reaction of ferredoxin-NADPq reductase by electrochemical methods", Bioelectrochemistry and Bioenergetics, 47, 1998, pp. 179-183). (Year: 1998).*

PCT Search Report and Written Opinion prepared for PCT/GB2017/060771, completed Apr. 27, 2017.

United Kingdom Search Report and Written Opinion prepared for GB1604671.6, completed Oct. 3, 2016.

Bandy, Jason, et al., "Electrophoretic Deposition of Titanium Oxide Nanoparticle Films for Dye-Sensitized Solar Cell Applications," 2011, Materials Sciences and Applications, No. 2, pp. 1427-1431.

Hitosugi et al., "$TiO_2$-based Transparent Conducting Oxide," physica status solidi (a), Jul. 1, 2010 (Jul. 1, 2010), pp. 1529-1537, Retrieved from the Internet: URL:http://www.apc.titech.ac.jp/~thitosugi/hitosugi/images/research/TNOreview.pdf.

Bachmeier, Andreas, et al., "How Light-Harvesting Semiconductors can Alter the Bias of Reversible Electrocatalysts in favor of H2 Production and CO2 Reduction," 2013, American Chemical Society, No. 135, pp. 15026-15032.

Bandy, Jason, et al., "Electrophoretic Deposition of Titanium Oxide Nanoparticle Films for Dye-Sensitized Solar Cell Applications," 2011, Material Sciences and Applications, No. 2, pp. 1427-1431.

Goren, Zafrir, et al., "Photocatalyzed Regeneration of NAD(P)H by CdS and TiO2 Semiconductors: Applications in Enzymatic Synthesis," 1988, Journal of Molecular Catalysis, No. 47, pp. 21-32.

* cited by examiner

SUBSTITUTE SHEET (RULE 26)

ELECTRODES

CROSS-REFERENCE TO RELATED APPLICATIONS

This application is a U.S. national phase of PCT/GB2017/050771, filed on Mar. 20, 2017, which claims priority to United Kingdom Patent Application No. 1604671.6, filed on Mar. 18, 2016, the disclosure of each of which is hereby incorporated herein by reference in their entirety.

BACKGROUND OF THE INVENTION

Field of the Invention

This invention relates to electrodes, methods of manufacturing and using the same and to chemical reactions achievable using said electrodes.

Description of Related Art

It is known that biocatalytic synthesis typically requires enzyme cofactors and that these enzyme cofactors are able to catalyse a huge number of industrially-relevant reactions with all the concomitant advantages that enzymes provide, including specificity and regioselectivity. A large number of such enzymes require nicotinamide cofactors (NADH and NADPH) cofactors for activity. Accordingly, there is a desire to produce nicotinamide cofactors for use in reactions. However, the high price of these cofactors means that stoichiometric usage of nicotinamide cofactors is prohibitively expensive. Thus to realise effective use of the cofactors it is necessary to find methods to regenerate cofactors, and preferably to regenerate the cofactors in situ.

It is known to drive the recycling of NAD/NADH using formate/formate dehydrogenase and alcohol/alcohol dehydrogenase. However, driving the recycling of the nicotinamide adenine dinucleotide phosphate (hereinafter NADP+) and its reducing agent NADPH, which we shall term the NADP+/NADPH couple, has proven to be more challenging. Hitherto the recycling of NADPH has been achieved using a two enzyme system that uses a kinase to catalyse phosphorylation of glucose to glucose-6-phosphate (G-6-P) and glucose-6-phosphate dehydrogenase to convert G-6-P to gluconic acid thereby to recycle NADPH. Whilst this does achieve recycling of the NADPH it also necessitates the consumption of the formate and glucose-6-phosphate. Accordingly, the presence of the second enzyme and chemicals for cofactor regeneration represent additional complications. Other methods of driving the NADP+/NADPH cycle include the use of (i) small electron-mediating molecules, such as methyl viologen, to transfer electrons from an electrode to an enzyme or (ii) organometallic (e.g. rhodium) complexes (e.g. Wu et al.; *Green Chem.* 2013; 15; 4, 1773-1789). However, the first process requires restricting the mediator to the electrode surface and the second process has low turnover numbers and also exhibits low selectivity. In this context, low selectivity is in relation to the NADPH species, which can be formed in either of two isomers (only one of which is usefully active—the isomer hydrogenated at the 1, 4 position) and may also form dimers (which are not active).

Accordingly, there is a desire to have a method to drive the recycling of nicotinamide cofactors, for example by driving the NADP+/NADPH couple to recycle NADPH, which exhibits one or more of the following: it does not require expensive chemical reagents; does not require subsequent removal of reagents before re-use; is selective; has large turnover numbers; and which may be deployed to effectively drive important industrially-relevant chemical reactions.

BRIEF SUMMARY OF THE INVENTION

A first aspect of the invention provides an electrode, the electrode comprising a substrate on which is located a porous layer of a conducting or semi-conducting oxide and having located thereon Ferredoxin NADP Reductase (FNR).

A second aspect of the invention provides a kit of parts for the recycling of nicotinamide cofactors, the kit comprising an electrode comprising a substrate on which is provided a porous layer of a conducting or semi-conducting oxide, and a solution of FNR for application to the porous layer.

A further aspect of the invention provides an electrode, the electrode comprising a substrate on which is located a porous layer of a conducting or semi-conducting oxide and having located thereon Ferredoxin NADP Reductase (FNR) and a co-enzyme.

The co-enzyme may be used to help drive a chemical reaction. Advantageously, by locating the co-enzyme on the porous layer the co-factor reaction path length can be minimized.

The conducting or semi-conducting oxide may be selected from one or more of indium tin oxide (ITO), fluorine doped tin oxide (FTO), $SrTiO_3$, $TiO_2$, doped $TiO_2$ or doped $ZrO_2$.

The porous layer may have a thickness of over 0.1, 0.2, 0.3, 0.4 or 0.5 µm, for example a thickness of over 0.6, 0.7, 0.8, 0.9 or 1.0 µm. In embodiments the thickness of the layer may be from 0.5 to 500 µm or 0.5 to 400, 300, 200, 100, 75, 50 40, or 30 µm, say from 0.5 to 25 µm, 0.5 to 20 µm, 0.5 to 15 µm, 0.5 to 10 µm or 0.5 to 5 µm. In an embodiment the porous layer has a thickness of from 0.75 to 10 µm, for example 0.75 to 7.5 µm say 0.75 to 5 µm. In another embodiment the porous layer has a thickness of 1 to 30 µm, 1 to 25 µm, 1 to 20 µm, 1 to 15 µm, 1 to 10 µm, for example 1 to 5 m. The pores of the porous layer may lie within the size range of 50-1000 nm, say from 50 to 900 nm or 800 nm. In at least some embodiments the pores in the porous layer may have sizes in the range of any one or 50, 60, 70, 80, 90 or 100 to any one of 1000, 900, 800, 700, 600 or 500 nm.

The porous layer may be formed from nanoparticles and/or from particles having an average diameter in the range of 10 to 1000 nm, for example in the range of 20 to 200 nm.

In embodiments the substrate may be electrically conductive and/or may comprise or may provide an electrically conductive layer. The substrate may be a self-supporting body. The substrate may comprise an inert support layer, for example on which the electrically conductive layer is located. The inert support layer may be formed from glass or a polymeric material.

In embodiments the substrate may be formed at least in part from carbon or metal, for example titanium. The electrically conductive layer may comprise carbon. In other embodiments the electrically conductive layer may be optically transparent or is substantially optically transparent. For example, the electrically conductive layer may comprise or be formed from a transparent conductive oxide (TCO). In embodiments the electrically conductive layer comprises ITO, FTO, aluminium-doped zinc oxide (AZO) or indium-doped cadmium oxide (ICO).

In one embodiment the substrate may comprise an electrically conductive foil, for example a metal foil, which may be formed from one or more of titanium, gold, silver, copper or other electrically conductive metals. A flexible foil substrate may be particularly attractive to allow a large substrate surface area in a relatively small volume. Suitable metal foils may have a thickness less than 1 mm, for example less than 0.9, 0.8, 0.7, 0.6, 0.5, 0.4, 0.3, 0.2 or 0.1 mm thick. In an embodiment, the metal foil may be folded or bent to shape (e.g. thereby to fill or better fill a reaction vessel). The metal foil may be provided with formations or may be deformed (e.g. to increase the available surface area thereof). In an embodiment, the metal foil may be wrapped in a metal wire, thereby to increase the surface area of the electrode surface. The metal foil may have a perimeter defining a surface area of $A_f$, the substrate (i.e the metal foil with the formations, wire and so on) may have a surface area of $A_s$, where $A_s > A_f$, for example by virtue of the presence of a metal wire or other formations or deformations. The deposition of conducting or semi-conducting oxide particles may occur after the metal foil has been wrapped by the wire, had formations applied or been deformed.

The electrode of the invention may form part of an electrochemical cell. The cell may be powered by a DC power supply or by, for example, a photocathode.

There is further provided, in a fourth aspect of the invention, a method of forming an electrode, the method comprising providing an electrically conductive substrate preform, securing particles of a conductive or semi-conducting oxide to the substrate preform to form a substrate and contacting the substrate with a solution of FNR.

The particles may be secured by physical application to the substrate. Alternatively, the particles may be secured to the substrate by electrophoretic deposition (EPD). The particles may be secured by heat annealing, for example at a temperature of 150 to 600° C., preferably in the range of 200 to 500° C. If the particles are secured by EPD we prefer not to heat anneal, although it is possible so to do.

A further aspect of the invention provides a method of reacting chemical components, the method comprising exposing a chemical to be reacted to a nicotinamide cofactor in the presence of an electrode, wherein the electrode comprises a porous conducting or semi-conducting oxide surface on which FNR has been located.

A yet further aspect of the invention provides a method of reacting chemical compounds, the method comprising exposing a chemical to be reacted to a nicotinamide cofactor which is immobilized on a porous layer of conducting or semi-conducting oxide, a reaction-specific co-enzyme also being immobilized on the porous layer.

The method may comprise exposing the chemical to be reacted to one of NADP+ or NADPH or, alternatively one of NAD+ or NADH.

In this specification the term 'nicotinamide cofactors' is intended to mean one of more of the NADP+/NADPH couple or the NAD+/NADH couple.

BRIEF DESCRIPTION OF THE SEVERAL VIEWS OF THE DRAWINGS

In order to better understand the invention, and by way of non-limiting example only, reference is made to the following drawings, in which.

DETAILED DESCRIPTION OF THE INVENTION

Figure 1:
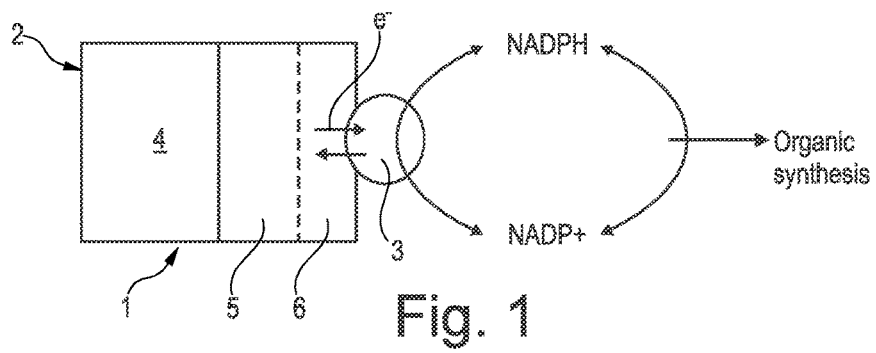
FIG. 1 is a schematic representation of the system of the invention.

Turning firstly to FIG. 1, there is shown an overall schematic representation of the invention, comprising a system 1 for conducting chemical reactions, the system 1 comprising an electrode 2 on which Ferredoxin NADP Reductase (hereinafter FNR) 3 is located. The electrode 2 comprises an optional substrate 4 and a conductive layer 5. The conductive layer 5 may be applied to the substrate 4 and/or the substrate 4 may comprise the same material as the conductive layer 5 (that is the substrate and conductive layer may be a single structure), the FNR being located on the conductive layer 5, as will be explained below.

To conduct a chemical synthesis, the electrode 2 is electrically coupled to a counter electrode (not shown) to form an electrochemical cell and is located in a solution of NADP+ with a further enzyme (for example a ketoreductase enzyme) and the chemical species to be reacted (for example a ketone). Applying an appropriate potential across the cell causes the FNR to drive the reaction of NADP+ to NADPH and thence a reaction of the further enzyme which subsequently drives organic synthesis, examples of which will be described below.

Figure 2A:
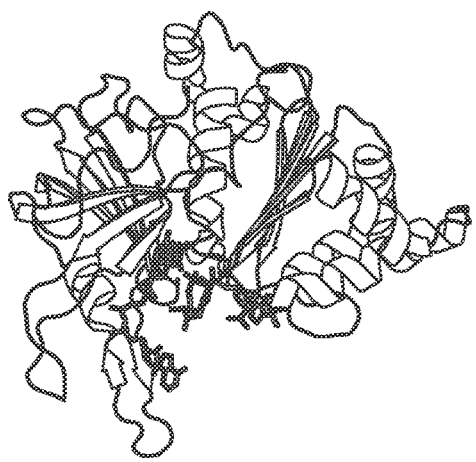
FIG. 2A is a schematic representation of the structure of FNR with a nicotinamide cofactor also bound.
Figure 2B:
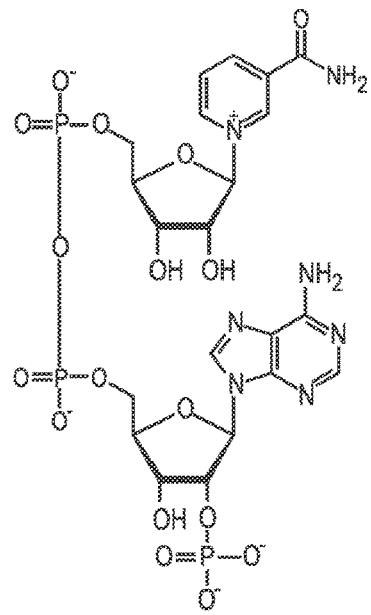
FIG. 2B is the chemical structure of NADP+.
Figure 2C:
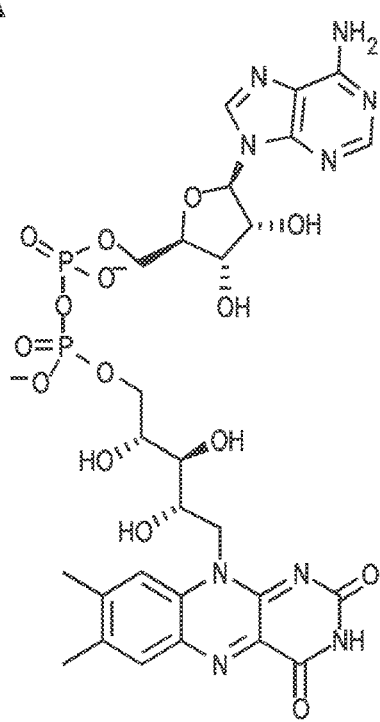
FIG. 2C is the chemical structure of flavin adenine dinucleotide (FAD)

For the purposes of exemplifying the invention the structures of each of FNR, NADP+ and flavin adenine dinucleotide (FAD—the cofactor of FNR) is shown in FIGS. 2A, 2B and 2C respectively.

We have surprisingly found that standard electrodes (e.g. those formed from graphite as are commonly and commercially available) are not usable for the purposes of the invention and that simple conductive oxide electrode materials, as are currently deployed in many distinct electrochemical applications (for example ITO glass slides as are commonly and commercially available), are not per se amenable to our invention and show vastly reduced in situ activity (and in some or many applications no activity at all), as compared to the electrodes of the invention.

Figure 4A:
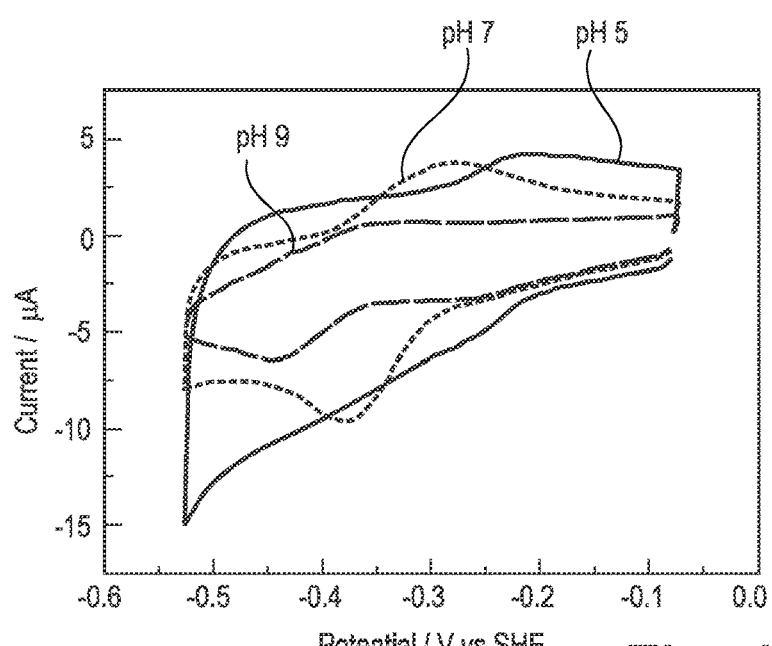
FIG. 4A is a series of cyclic voltammograms of an electrode of the invention (potential scale vs a standard hydrogen electrode (SHE)) at various solution pH.
Figure 4B:
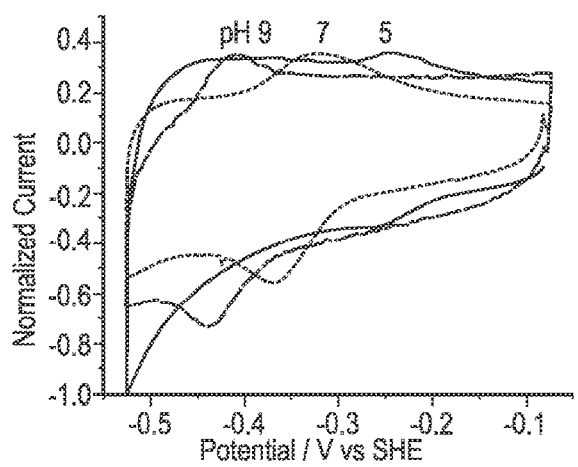
FIG. 4B is a series of cyclic voltammograms of an electrode of the invention in the absence of NADP+ vs a SHE at various solution pH.
Figure 4C:
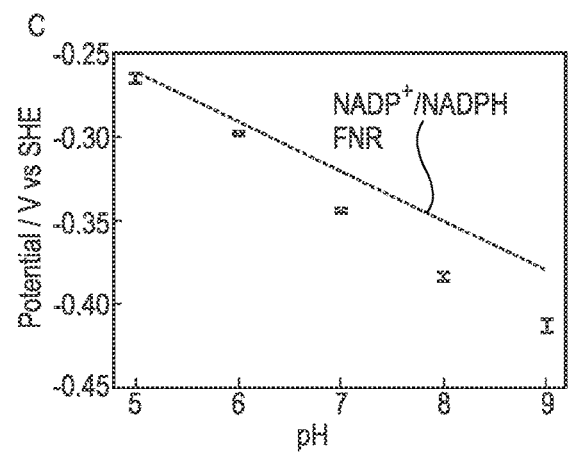
FIG. 4C is a graph showing the pH dependence (i) of the average potentials for the non-turnover signals due to the FAD, and (ii) of the thermodynamic reduction potential of the NADP+/NADPH couple.

The redox potential of NADP+/NADPH (vs SHE at pH7) is −0.32V (see FIG. 4C). We have found that when deploying a plain or bare indium tin oxide (ITO) electrode to which FNR has been added, and at the appropriate potential range, NADP+ does not react. We believe that this is because the FNR does not bind to the flat ITO layer and so washes into the solution where it is unable to do useful work. A similar problem was found with plain graphite electrodes which also showed no activity.

We have solved this issue by ensuring that the conductive layer 5 is provided with a porous face layer 6. Although we neither wish, nor intend, to be bound by any particular theory, we believe that such a porous layer 6 allows for a larger macroscopic surface area and hence binding sites for the FNR. Indeed, when the porous face layer 6 is formed using nanoparticles, the micro-morphological surface is rough, thereby providing a greater number of potential binding sites. Further, the FNR may adsorb better on the porous surface due to the presence of a slight negative charge from surface hydroxyl groups. The FNR may also form reservoirs within the pores of the electrode 2 and have sufficient mobility to continually drive the NADPH/NADP+ couple reaction cycle.

Figure 3:
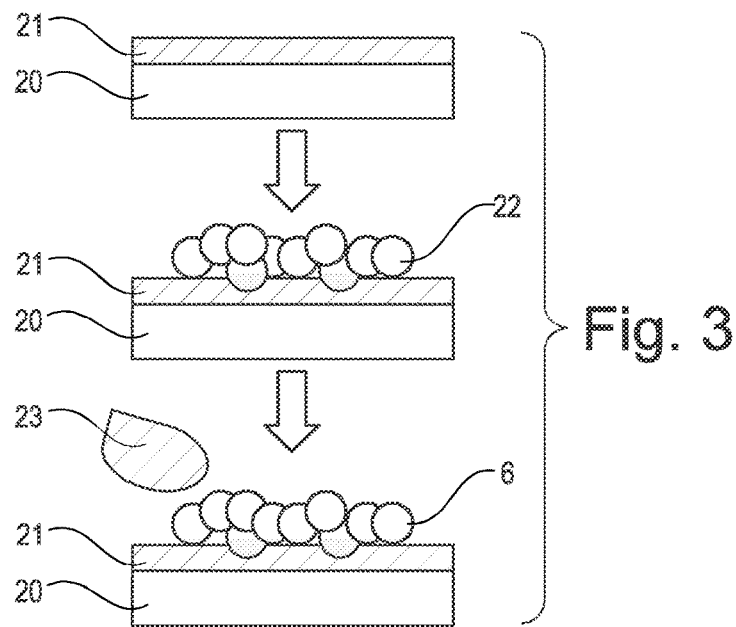
FIG. 3 is a schematic representation of the formation of an electrode according to the invention.

Reference is now made to FIG. 3 which provides a step-wise schematic of the formation of an electrode 2 according to the invention, wherein a substrate 20, for example a glass substrate 20, provided with a thin conductive layer 21 (for example (ITO) has deposited thereon particles 22 of the conductive oxide (or indeed another conductive or semi-conductive oxide). The particles are or may be calcined or annealed in an oven (or otherwise secured) to ensure that there is sufficient contact and binding. The particles 22 provide a porous face layer 6. A solution of FNR 23 is then added dropwise (or otherwise) to the porous face layer 6 and allowed to dry.

Figure 3A:
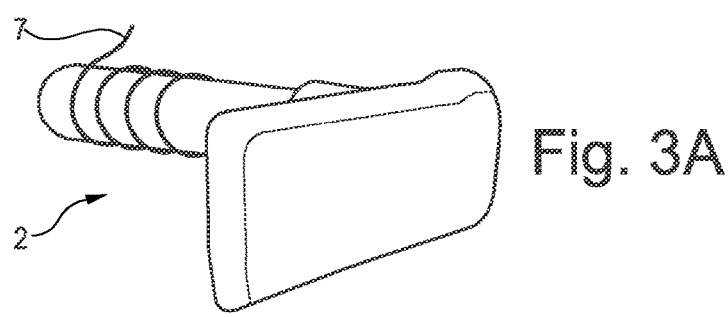

To complete the electrode 2 a copper wire 7 (or other conductive wire) is attached to the conductive layer 5 using a conductive adhesive material (as seen in FIG. 3A).

To further exemplify the invention, reference is also made to the following non-limiting Examples:

Example 1a—Preparation of ITO Electrodes i. Preparation of Conductive Glass Slides.

Cut ITO-coated glass slides (SPI Supplies) into approximately 2.5 cm×1.0 cm pieces. Clean glass slides by sonication in acetone, ethanol, and water, respectively for 15 mins each. Leave to dry in air.

ii. Doctor Blade Method

Make ITO powder suspension by adding 0.05 g ITO powder (Sigma) to 53 µL acetic acid and 143 µL ethanol. Sonicate for 30 mins.

Secure glass slides to paper, using adhesive tape, marking out the area to be loaded. Make sure the conductive face is uppermost. Pipette 20 µL of ITO powder suspension onto exposed area. Use another glass slide to spread the ITO suspension and remove any excess suspension, making the ITO layer level with the adhesive tape thickness. Leave to dry.

iii. Calcining the Slides (Optional)

Calcine the ITO-loaded slides at 450° C. for 30 min to ensure good contact.

iv. Making ITO Slides into Electrodes

Attach a copper wire to the conductive side of the glass slide with silver glue. Cover any exposed surfaces with resin. Leave to dry overnight.

v. Applying FNR

Drop FNR solution (50-200 µM, 1-20 µL—Enzyme code number EC.1.18.1.2) onto the surface of the ITO electrode. Leave to partially dry for 1-3 mins.

Example 1b—Preparation of ITO Electrodes i. Preparation of Conductive Glass Slides.

Cut ITO-coated glass slides (SPI Supplies) into approximately 2.5 cm×1.0 cm pieces. Clean glass slides by sonication in acetone, ethanol, and water, respectively for 15 mins each. Leave to dry in air.

ii. Electrophoretic Deposition Method

Put 0.01 g ITO powder (Sigma) and 0.005 g $I_2$ into 25 mL acetone. Sonicate for 1 hour. Put 2 conductive glass slides parallel to each other, approximately 1 cm apart, with facing conductive sides. Apply 10 V for varying amounts of time (0.5-10 mins). The ITO powders become positively charged in the solution, and will be attached to the negative electrode. The amount of loading can be controlled by changing the applied voltage and time.

iii. Calcining the Slides (Optional)

Calcine the ITO-loaded slides at 450° C. for 30 min to ensure good contact.

iv. Making ITO Slides into Electrodes

Attach a copper wire to the conductive side of the glass slide with silver glue. Cover any exposed surfaces with resin. Leave to dry overnight.

v. Applying FNR

Drop FNR solution (50-200 µM, 1-20 µL—Enzyme code number EC.1.18.1.2) onto the surface of the ITO electrode. Leave to partially dry for 1-3 mins.

Example 1c—Preparation of ITO Electrodes i. Preparation of Electrodes.
Provide a pyrolytic graphite edge plane electrode (PGE) or a length of titanium foil (0.8 mm thick, Sigma)

ii. Electrophoretic Deposition Method
Add ITO powder (0.02 g, Sigma) and $I_2$ (0.005 g, Alfa Aesar) to acetone (25 mL, Sigma). Sonicate for 30 minutes. Locate two conductive substrates parallel to each other, separation 1-2 cm. Apply 10 V for varying amounts of time (3-6 minutes). The ITO powders become positively charged in the solution, and will be attached to the negative electrode. The amount of loading can be controlled by changing the applied voltage and time.

iii. Drying the Electrodes
The electrodes were left in the air to dry.

iv. Making Electrodes
Attach a copper wire to the electrode with silver glue. Cover any exposed surfaces with resin. Leave to dry overnight.

v. Applying FNR
Drop FNR solution (e.g. 0.2 mM, 0.5-3 µL—Enzyme code number EC.1.18.1.2) onto the surface of the ITO electrode. Leave to partially dry for 1-3 mins. Rinsed with water.

Example 1d—Preparation of ITO Electrodes i. Preparation of Electrodes.
Provide a length of titanium foil (0.127 mm thick, Sigma) and wrap a length of titanium wire around the foil (0.25 and/or 0.81 mm).

ii. Electrophoretic Deposition Method
Add ITO powder (0.02 g, Sigma) and $I_2$ (0.005 g, Alfa Aesar) to acetone (25 mL, Sigma). Sonicate for 30 minutes. Locate two conductive substrates parallel to each other, separation 1-2 cm. Apply 10 V for varying amounts of time (3-6 minutes). The ITO powders become positively charged in the solution, and will be attached to the negative electrode. The amount of loading can be controlled by changing the applied voltage and time.

iii. Drying the Electrodes
The electrodes were left in the air to dry.

iv. Making Electrodes
Attach a copper wire to the electrode with silver glue. Cover any exposed surfaces with resin. Leave to dry overnight.

v. Applying FNR
Drop FNR solution (e.g. 0.2 mM, 0.5-3 µL—Enzyme code number EC.1.18.1.2) onto the surface of the ITO electrode. Leave to partially dry for 1-3 mins. Rinsed with water. In this Example the available surface area for the ITO powder to adhere to the substrate surface was significantly increased by the wire.

In all experiments 1a, 1b, 1c and 1d the ITO powder consisted of or comprised nanoparticles with an average diameter of 50 nm.

We believe that the FNR forms a dense electroactive film on the ITO. It was found that using the electrophoretic deposition method it was not necessary to anneal the ITO layer, thereby further reducing the processing steps required and making construction simpler and cheaper than would otherwise be the case.

Example 2—Demonstrating Efficacy

Referring to FIG. 4a, a series of cyclic voltammetry experiments were undertaken at different pH, with an electrode of the invention fabricated in accordance with Example 1A above. The experiment sought to show the activity of the electrode of the invention in the presence of NADP+.

A solution was made containing MES buffer and NADP+ (100 µM).

The electrode was inserted into the solution and the voltage swept at 5 mVs$^{-1}$.

The results clearly show that the FNR is active in the pH range of the experiment, i.e. between pH 5 and pH 9, with a maximum of activity at or around pH 7. Indeed, we believe that maximum activity is at or around pH 8.

To determine the effect in the absence of NADP+, we conducted a further set of experiments (as seen in FIG. 4b) in which the absorbed FNR demonstrates non-turnover peak like signals from, we believe, the FAD cofactor. These can be used to determine the amount of electroactive FNR absorbed. The FAD signals for oxidation and reduction are sharp because the electrochemical reaction is a two-electron process. The pH-dependent FAD redox potential in FNR is also unusually negative. These two properties provide an important marker over time and allow for an unambiguous assessment of FNR stability.

Figure 4D:
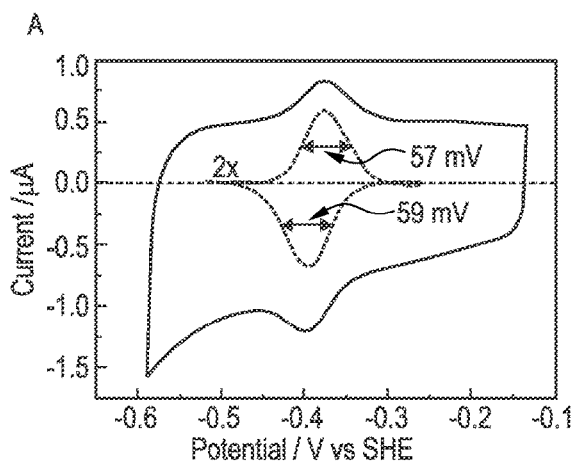
FIG. 4D is a cyclic voltammogram of an electrode of the invention in the absence of NADP+, together with a background subtracted signal.

Referring to FIG. 4D, there is shown a cyclic voltammogram of an electrode of Example 1c (PGE) in the absence of NADP+. Reduction peaks are visible at approximately −0.38V vs SHE at pH 8, which, we believe are due to the FAD group in FNR. The peaks are referred to as non-turnover signals. The ideal peak width at half maximum height for an immobilized redox couple is 89/n mV at 20° C., where n is a coefficient reflecting the number of electrons transferred cooperatively. As evident from FIG. 4D the peak widths are 57-59 mV in each direction indicating that two electrons are transferred with considerable cooperativity.

Figure 4E:
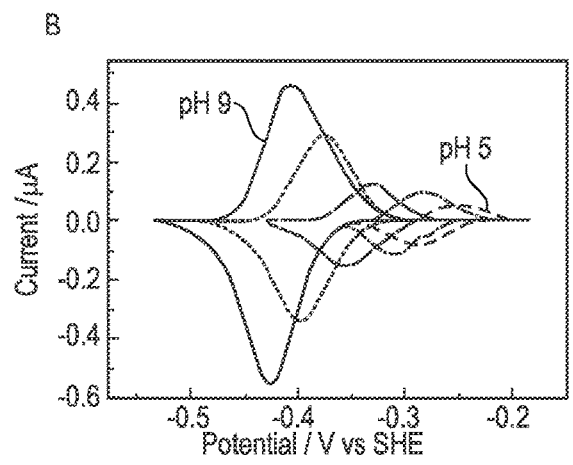
FIG. 4E is a series of background subtracted signals of cyclic voltammograms of an electrode of the invention as pH is varied.

The area under the background-subtracted current represents the total charge passed and is proportional to the amount of electroactive FNR adsorbed onto the electrode. Using the electrode of Example 1c (PGE), experiments were performed to determine how coverage varies with pH, applying the same amount of FNR in each case. FIG. 4E shows the non-turnover signals of FNR on ITO electrodes obtained in the pH range 5 to 9. In each case the half-height peak widths lie in the range 56 to 64 mV in either direction, showing that two-electron cooperativity occurs over the entire pH range. Strikingly, the results demonstrate a strong dependence of coverage with pH, with higher coverage at higher pH. It was also shown that FNR has a high affinity from ITO when applied at pH 9, adsorbing to a level exceeding 500 pmol cm$^{-2}$. Surprisingly, when the electrode was transferred to a solution at pH 5 the coverage decreased but was largely restored upon being returned to a solution of pH 9. In contrast, when FNR was applied at a pH of 5, coverage did not increase when the electrode was transferred to a solution of higher pH. The diameter of FNR is approximately 6 nm and so an ideal monolayer coverage (assuming a planar surface) would be ca. 5 pmol cm$^{-2}$. The high coverage of ca. 100 monolayers must be due to the porous structure of the ITO surface. From these results and from the results of FIGS. 4D and 4E, we conclude that binding of FNR within the pores involves (a) general permeation that is more favourable at high pH and (b) localized binding in an electroactive configuration which is also stronger at higher pH. Lowering the pH therefore causes some enzyme molecules to become more loosely bound, but most remain buried within the pores, so that restoring the high or higher pH conditions causes the entrapped enzyme molecules to re-bind.

FIG. 4c shows the non-turnover signals of FNR, obtained from cyclic voltammograms recorded in the pH range 5 to 9 (data points), with the reduction potential of the NADP+/NADPH couple (solid line). The NADP+/NADPH couple has a reduction potential of −0.32 vs SHE at pH 7, with a slope of −30 mV per pH unit. In this pH range the reduction potential of FNR is always more negative than that of NADP+, the difference increasing with pH. The data show that FNR is biased slightly to favour NADP+ reduction. Analogous results were obtained with electrodes produced according to Examples 1a and 1b, as well as with electrodes formed in accordance with Example 1d (titanium foil, 0.8 mm Sigma).

Example 3—Demonstrating the Effect of NADP+

Figure 5A:
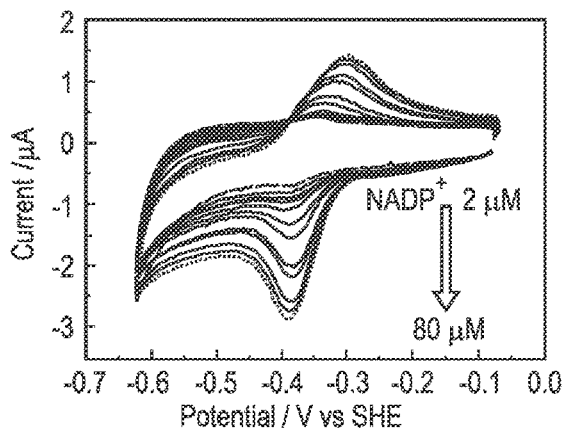
FIG. 5A is a series of cyclic voltammograms of an electrode of the invention vs a standard hydrogen electrode (SHE) at various NADP+ concentrations.

Referring now to FIG. 5A, a series of cyclic voltammetry experiments were undertaken with different amounts of NADP+, using an electrode fabricated in accordance with Example 1a above. The experiments sought to show the activity of the electrode of the invention in the presence of various amounts of NADP+.

A solution was made of MES buffer and NADP+ (2 to 80 µM).

The electrode was inserted into the solution and the voltage swept at 5 mVs$^{-1}$.

The results clearly show that the current response is dependent upon NADP+ concentration, with a higher response at higher NADP+ loading.

Figure 5B:
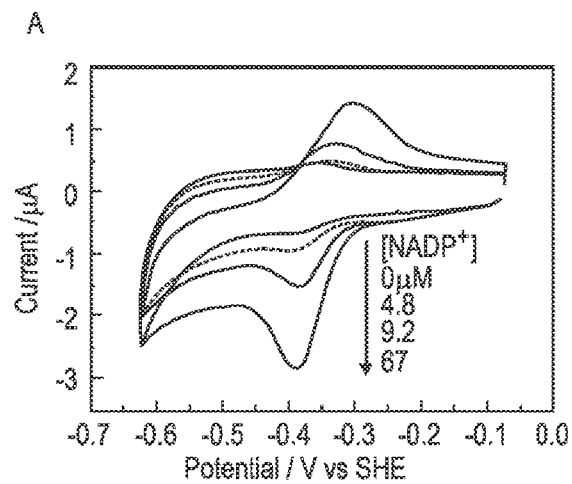
FIG. 5B is a series of cyclic voltammograms of an electrode of the invention vs a standard hydrogen electrode (SHE) at various NADP+ concentrations.

Referring now to FIG. 5B, a series of cyclic voltammetry experiments were undertaken with different amounts of NADP+, using an electrode fabricated in accordance with Example 1c above (PGE). The experiments sought to show the activity of the electrode of the invention in the presence of various amounts of NADP+ at pH 8.

A solution was made of MES buffer and NADP+ (4.8 to 67 µM).

The electrode was inserted into the solution and the voltage swept at 5 mVs$^{-1}$.

The results clearly show that the current response is dependent upon NADP+ concentration, with a higher response at higher NADP+ loading.

Both results show that upon adding NADP+ to the cell an enhanced reduction current is observed and on the return scan the resulting NADPH is oxidized. Accordingly, the FNR adsorbed on the ITO surface is active for cofactor regeneration in both directions.

Example 4A—Demonstrating Efficacy with Other Materials

Figure 6A:
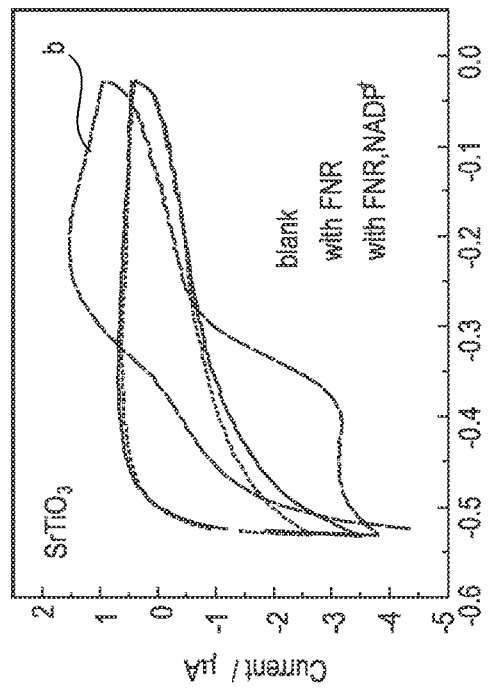
FIGS. 6A, 6B, 6C and 6D each show cyclic voltammograms of an electrode made in accordance with the invention.
Figure 6B:
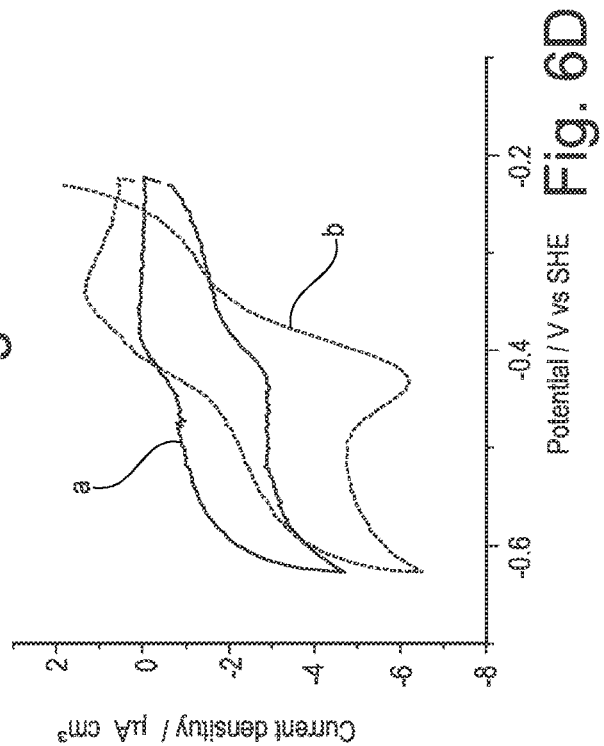
Figure 6C:
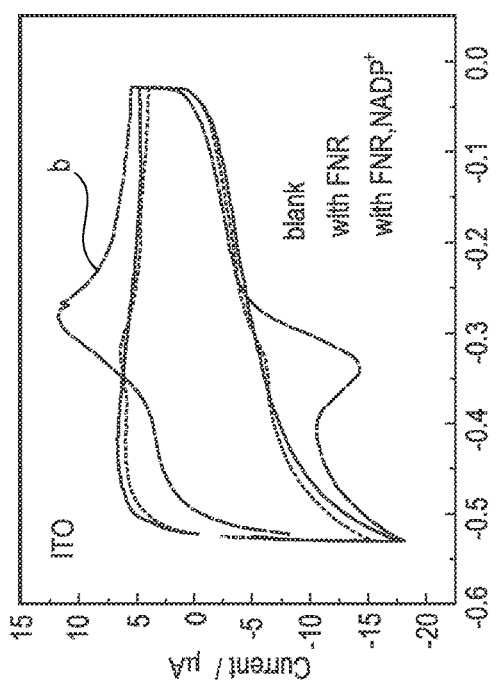

In order to demonstrate that the invention is broadly applicable across many types of porous conducting or semi conducting layers we constructed three electrodes in accordance with Example 1a (i.e. upon a plain glass/ITO substrate), the first used ITO nanoparticles (FIG. 6A), the second used strontium titanate (SrTiO$_3$) nanoparticles of approximate average diameter 100 nm (FIG. 6B), and the third zirconia (ZrO$_2$) nanoparticles of approximate average diameter of 100 nm (FIG. 6C).

In each case the experiment was carried out:
(i) without the addition of FNR to the electrode;
(ii) with FNR but in the absence of NADP+;
(iii) with FNR and in the presence of NADP+ (120 µM) (line b in each case).

As will be appreciated, in each case activity was demonstrated only with the addition of FNR and in the presence of NADP+, clearly demonstrating efficacy across a wide range of porous layer chemistries.

The results with strontium titanate nanoparticles and zirconia are particularly striking, not least because both of these species are actually semi-conductors. From an analysis of the data (particularly when there is no NADP+ present) we can see no evidence of non-turnover peaks from the voltammograms, indicating that the amount of electroactive FNR is below the detection limit, but these few enzyme molecules must be highly active with respect to reaction with NADP+. Although we neither wish not intend to be bound by any particular theory, we believe that this indicates that the active FNR is located at the junction between the ITO substrate and the respective semi-conductor at the base of large pores. If this is correct, porosity and conductivity must play a significant part in the activity of the electrode.

Example 4B—Demonstrating Efficacy with Further Materials

Figure 6D:
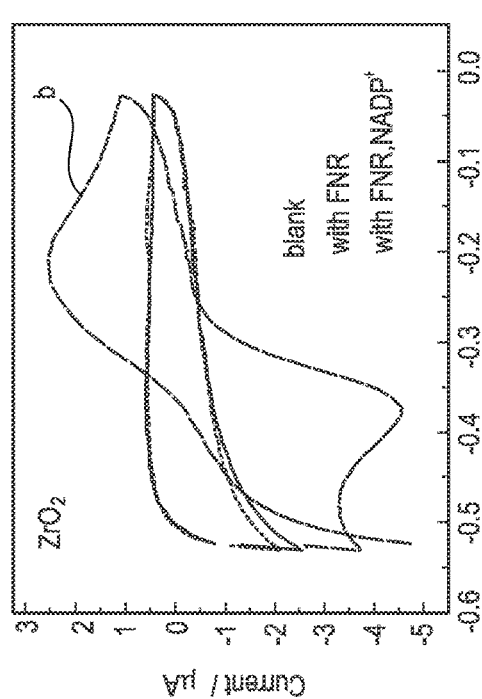

In order to demonstrate that the invention is broadly applicable across many types of porous conducting or semi conducting layers we constructed three electrodes in accordance with Example 1a (i.e. upon a plain glass/ITO substrate) and used FTO nanoparticles (FIG. 6D).

In this case the experiment was carried out:
(i) with FNR but in the absence of NADP+ (line a)
(ii) with FNR and in the presence of NADP+ (50 µM) (line b).

As will be appreciated, in this case activity was demonstrated only with the addition of FNR and in the presence of NADP+, clearly demonstrating efficacy across a wide range of porous layer chemistries.

Example 5—Demonstrating Production of NADPH

In order to show that the electrodes of the invention do, in fact, generate NADPH from the NADP+ located in solution an electrode of the invention, made in accordance with Example 1a, was located in a solution of NADP+. The electrode was energized for 20 hours (t=20). Ultraviolet (UV-vis) spectra were taken of the solution at t=0 and t=20 to detect the presence of NADPH (λ−340 nm).

Figure 7:
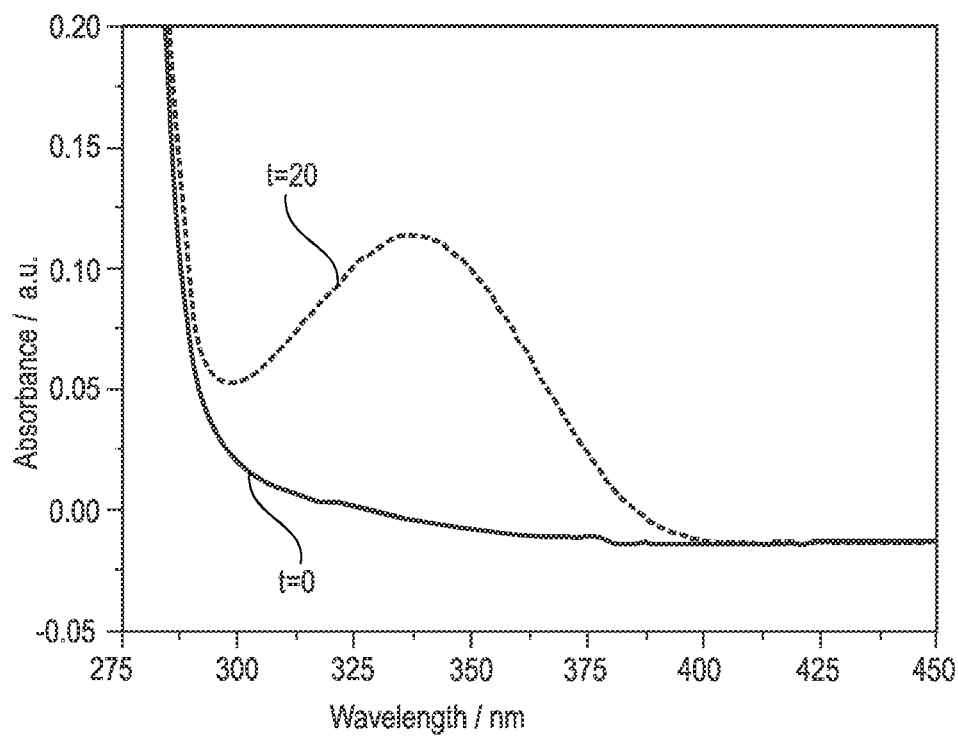
FIG. 7 shows the results of experiments to demonstrate the production of NADPH.

The results are shown in FIG. 7.

As can be clearly seen from the growth of the absorption peak at 340 nm, a significant amount of NADPH has been produced.

Indeed, from the UV absorption data we calculate that there was 0.17 µmol in 6 mL. This is in exceedingly good agreement with the calculation based on total charge passed in the experiment, which gave a value of 0.18 µmol in 6 mL.

The results indicate that there was a 14% conversion of NADP+ present in the solution.

Example 6—Calculation of Turnover Number

As stated above, see Example 2, the non-turnover peak area can be used to calculate the amount of electroactive FNR adsorbed on the electrode of the invention (peak area is proportion to concentration).

Figure 8:
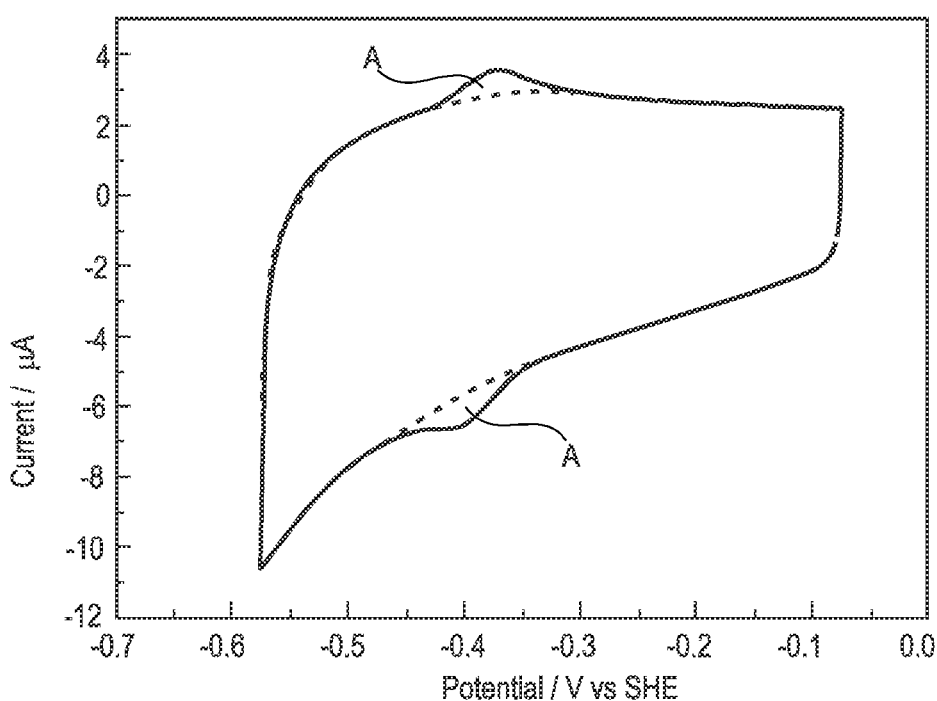
FIG. 8 is a cyclic voltammogram to determine non-peak turnover area.

A relatively rapid voltage scan experiment was conducted to determine non-turnover peak area (see FIG. 8). The area of the peak, indicated by A on FIG. 8, is proportional to the amount of FNR at the surface of the porous layer.

In this experiment the electrode of the invention (see Example 1a), was placed in MES buffer (pH 8, 15° C.) and the voltage scanned at 30 mVs$^{-1}$.

From this data we calculate the turnover number to be 23000 and the turnover frequency (averaged over 20 hours) to be 0.3 s$^{-1}$.

However, we understand that the electrochemical reduction of NADP+ is diffusion controlled and so only those molecules bound closest to the bulk solution interface will contribute to catalysis. Assuming the electrode surface is packed to capacity with FNR molecules the immediately accessible surface coverage is estimated to be 5 μmol cm$^{-2}$ which leads to a revised TOF of at least 40 s$^{-1}$. In support of this model, a shoulder is sometimes visible on the oxidative scan, located negative of the oxidation peak for NADPH. From its position the shoulder corresponds to the FNR oxidative non-turnover signal, and it may be assigned to FNR molecules that are buried and thus redundant with regards to immediate catalytic activity. The shoulder fades in comparison to the main peak as the scan rate is decreased (slow conditions favour oxidation of diffusing NADPH) and is not visible on the reductive scan because its position is more negative than the NADP+ reduction potential.

We believe that the electrodes of the invention are beneficial for many reasons, not least because of the simplicity of fabrication, the simplicity of action, the high selectivity and the ability to actively generate NADPH in situ and to drive the NADP+/NADPH couple to generate useful chemical work in an allied or coupled reaction scheme.

Figure 9A:
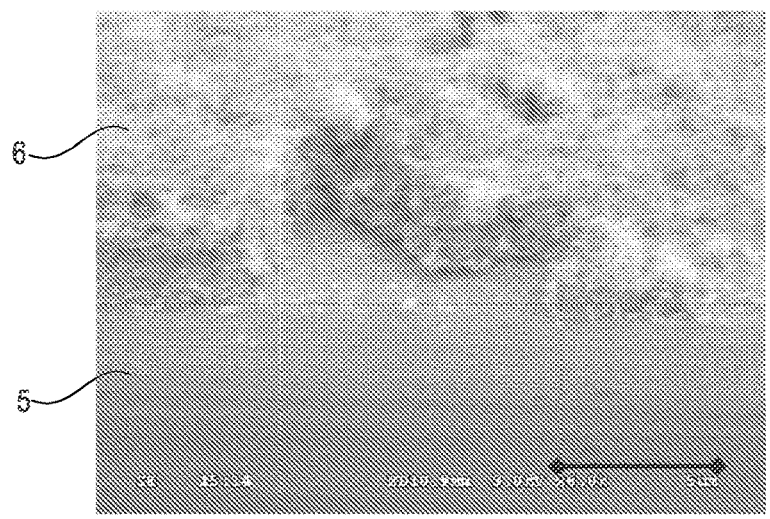
FIGS. 9A, 9B and 9C are a series of SEM micrographs of the porous layer of an electrode of the invention.
Figure 9B:
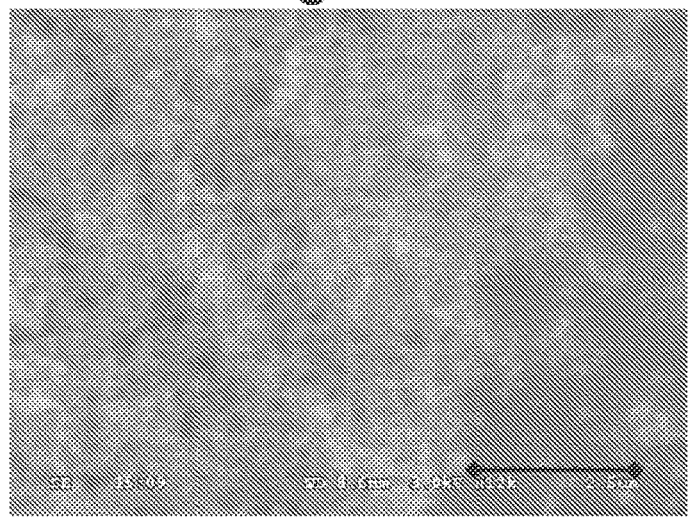

The porous structure of the porous layer 6 is shown in FIG. 9A where it is clearly seen that an electrode of the invention 2 (made in accordance with Example 1A) has a porous layer 6 located on an ITO conductive layer 5 (FIG. 9A, the scale bar is 5 μm). The porous layer has a thickness in the range of 1 to 5 μm. We believe that porous layers within the scope of the invention may have thicknesses in the range of 0.25 or 0.5 to 30 μm. Referring to the plan view of the porous layer as seen in FIG. 9B, as the magnification increases (FIG. 9B, scale bar 2.5 μm) the nature of the porosity can start to be determined.

Figure 9C:
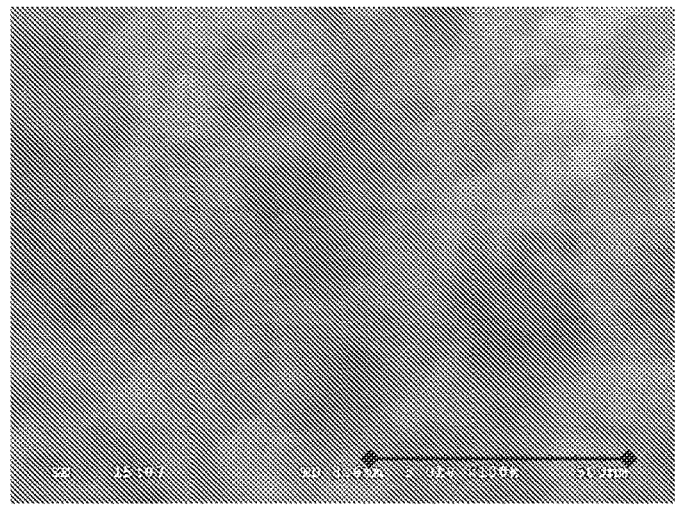

Referring now to FIG. 9C, as the magnification increases further (FIG. 9C, the scale bar is 500 nm) the structure of the porous layer, and its formation from nanoparticles, can be determined clearly as well as the nature of the porosity within the porous layer.

We believe that pore sizes in the range of 50 to 1000 nm are useful for carrying out the invention.

In order to demonstrate further that it is not necessary to have an inert (non-electrically-conductive) substrate but instead the substrate can itself be conductive we conducted the following experiment:

Example 7—Alteration of Substrate

An electrode was made using the methodology of Example 1A but in place of an ITO/glass slide a graphite disc electrode was deployed.

Figure 10:
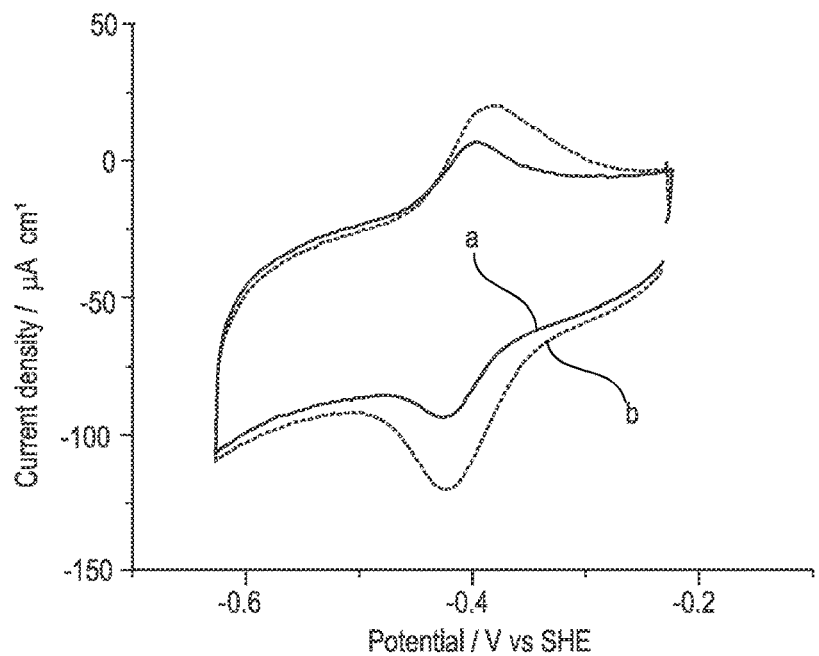
FIG. 10 is a is a cyclic voltammogram of a further electrode of the invention.

A series of cyclic voltammogram experiments were conducted (FIG. 10).

In this case an experiment was carried out:
(i) with FNR but in the absence of NADP+ (line a)
(ii) with FNR and in the presence of NADP+ (50 μM) (line b).

As will be appreciated, in this case activity was demonstrated with the addition of FNR and in the presence of NADP+, clearly demonstrating further that a conductive substrate of completely distinct chemistry can be deployed with conductive and semi-conducting nanoparticles to form an electrode of the invention.

Clearly, the invention may be deployed with inert (non-electrically conductive) substrates which are provided (e.g. coated) with a conductive layer, and also with conductive substrates (for example those made from graphite or metal). Where the substrate in inert, it will be provided or coated with a conductive material which may be selected from ITO, FTO or other conductive refractory materials. In any case, the active surface of the so-formed electrode will be provided by a porous conducting or semi-conducting material. The substrates may be rigid or flexible.

Figure 11:
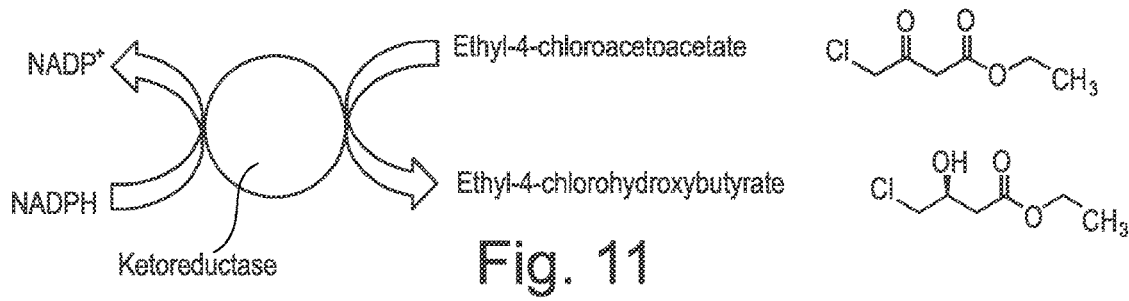
FIG. 11 is a schematic representation of a coupled reaction.

Referring now to FIG. 11, there is shown the NADP+/NADPH couple mediated reaction of a ketoreductase enzyme of the reduction of a ketone to an alcohol. Clearly, as the electrode of the invention is able to generate significant amounts of NADPH it can be used to drive the corresponding conversion of the ketone to the alcohol.

In order to demonstrate the capability of electrodes of the invention and the ability to drive industrially-relevant chemical reaction, reference is made to the following, non-limiting, Examples.

Example 8—In Situ Organic Synthesis

Figure 12:
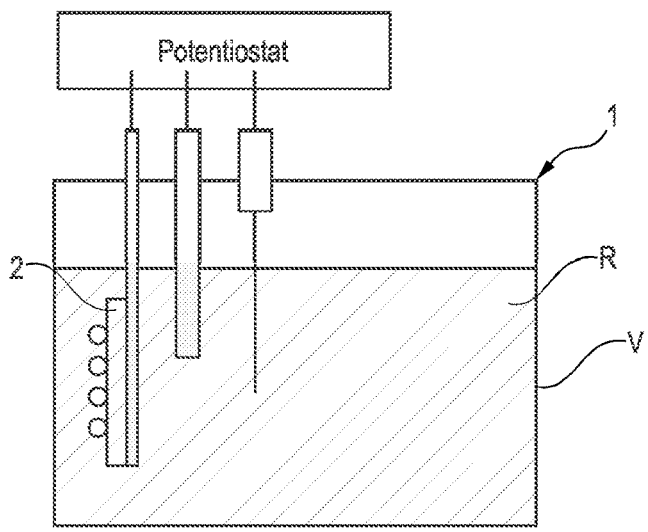
FIG. 12 shows a schematic set-up of a system according to the invention.

A system, in accordance with the invention, was set up, as shown in FIG. 12, with an electrochemical cell located within a reaction vessel V. The electrochemical cell comprised an electrode 2 of the invention. Located within the reaction vessel are the reactants R, namely in this instance, NADP+ (5 μM), ethyl-4-chloroacetoacetate (10 mM) and ketoreductase (3 units, where 1 unit corresponds to the amount of enzyme which reduces 1 mol of ethyl-4-chloroacetoacetate at pH 6 and 25° C.) The bulk of the reaction solution was MES buffer (pH7, 15° C.).

The applied potential was −0.52 V vs SHE (180 mV overpotential relative to NADP+ reduction potential).

Figure 13A:
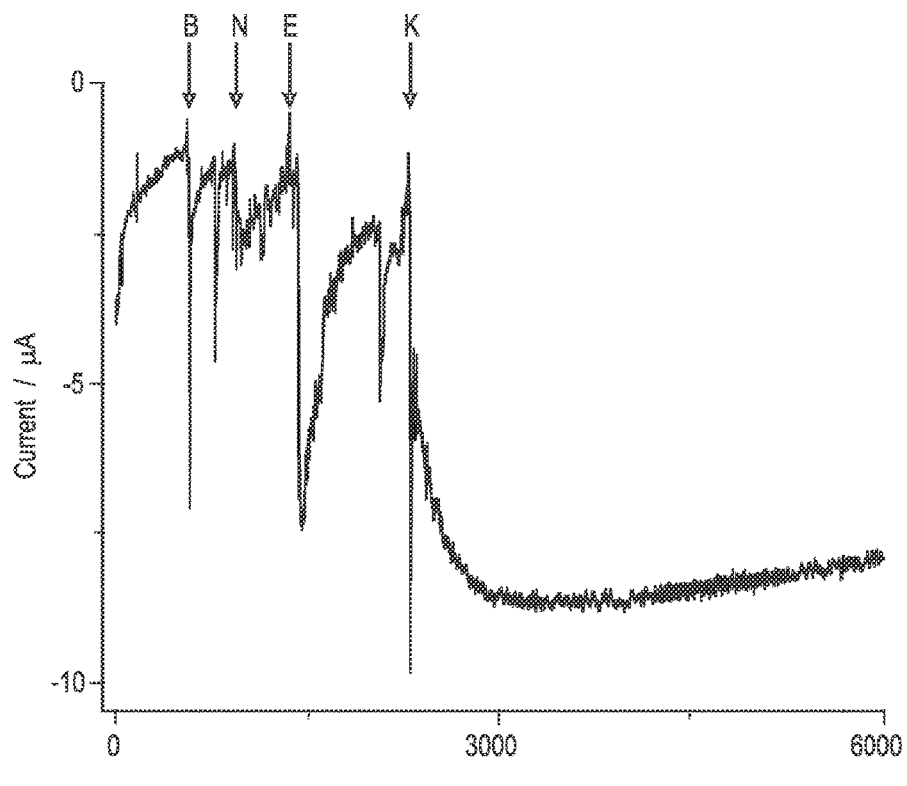
FIGS. 13A and 13B show chronoamperometry scans of reactions utilizing the invention.
Figure 13B:
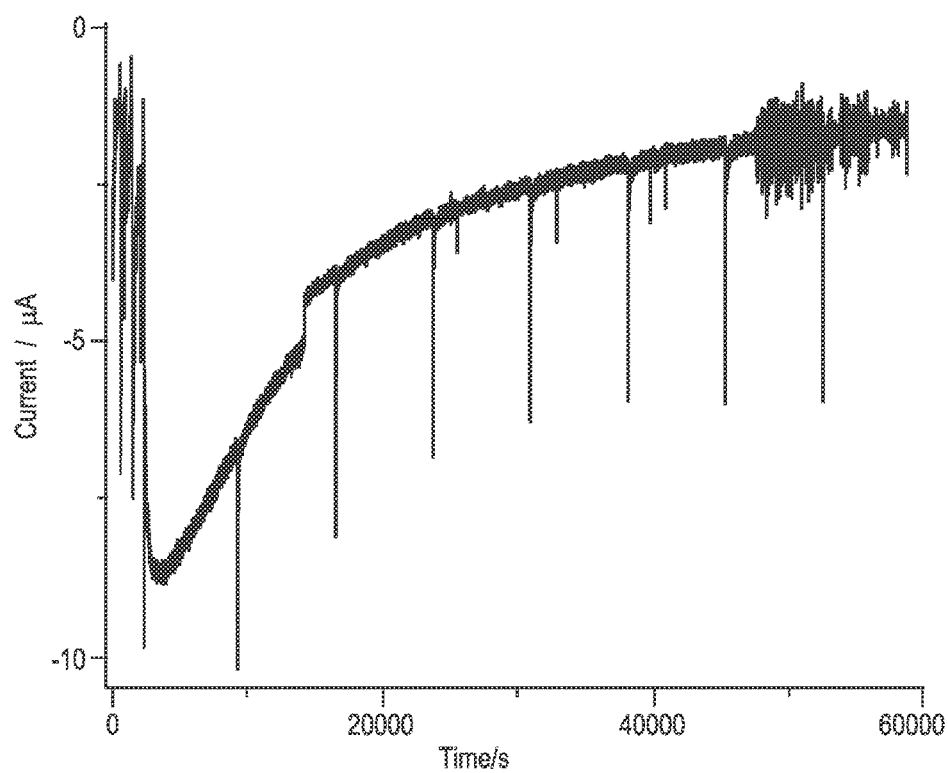

Referring to FIGS. 13A and 13B, there is shown chronoamperometry traces for the first 1.6 hours (FIG. 13A) of a 16 hour run (FIG. 13B).

The arrows indicate the presence of buffer (B), NADP+ (N), ethyl-4-chloroacetoacetate (E), and ketoreductase (K).

Figure 14A:
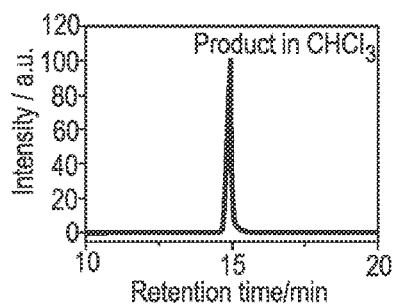
FIGS. 14A, B and C show GC-MS data in relation to a reaction utilizing the invention.
Figure 14B:
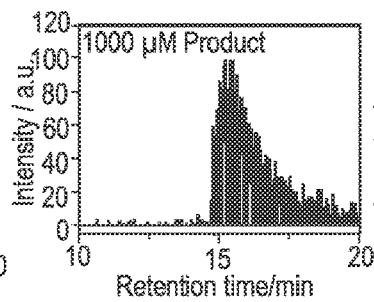
Figure 14C:
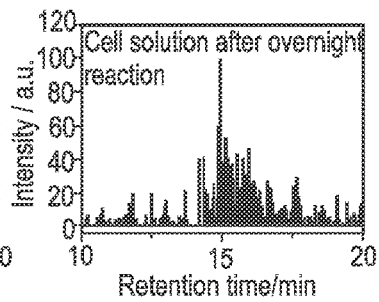

In order to demonstrate that product had been made GC-MS scans were taken of the desired product (FIG. 14A), the solution from the cell prior to reaction (FIG. 14B) and the solution from the cell after reaction (FIG. 14C)

Our analysis from the GC-MS data indicated that the amount of product is at least twice that of the starting NADP+ concentration, indicating that the system turns over at last three times.

We believe that upon optimisation of the electrode we will be able to demonstrate much greater system turnover amounts. Without wishing or intending to be bound by any particular theory, we believe that the reaction pathway involves a steric competition between FNR and NADP+ at the porous conductive layer which can reduce the turnover of NADP+. By optimizing pore size and amount (which may involve one or both of macroporosity of the layer and microporosity of the particles) and optimization of the amount of FNR we will be able to drive significant turnover of the system. We believe that layer thicknesses and pore sizes as set out above are effective in the invention. Further in situ organic synthesis experiments have demonstrated improved turnover numbers, as shown below:

Example 9A—In Situ Organic Synthesis

A system, in accordance with the invention, was set up, as shown in FIG. 12, with an electrochemical cell located within a reaction vessel V. The electrochemical cell comprised an electrode 2 of the invention formed in accordance with Example 1c (PGE, area 0.3 cm$^2$).

Figure 15A:
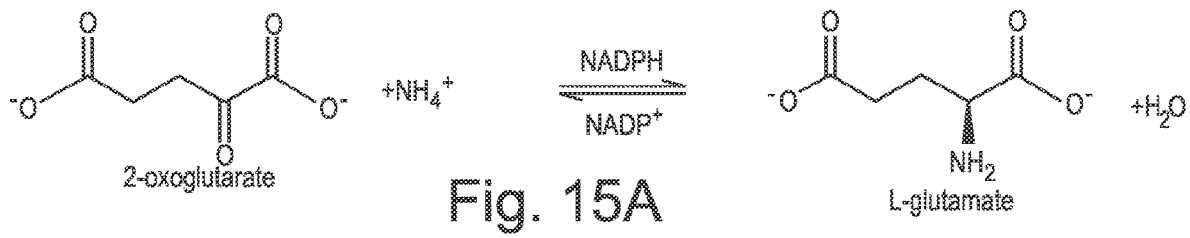
FIG. 15A shows a reaction scheme of 2-oxoglutarate.

This experiment was arranged to investigate the conversion of 2-oxoglutarate to L-glutamate (see FIG. 15A) catalyzed by glutamate dehydrogenase (GLDH).

Figure 15B:
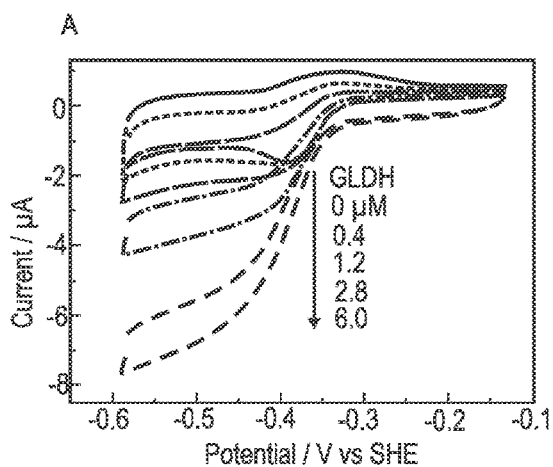
FIG. 15B is a series of cyclic voltammograms of an electrode of the invention vs a standard hydrogen electrode (SHE) at various GLDH concentrations.

With the electrode in place and the reactants ((NH$_4$)$_2$SO$^4$ 10 mM, 2-oxoglutarate 10 mM) in place, NADP+ was added to the cell and the expected NADP+/NADPH reduction/oxidation currents were recorded (see FIG. 15B). Additions of GLDH (0.4 to 6.0 µM final concentration) caused the oxidation and reduction peaks to convert to sigmoidal reduction waves, the intensity of which increasing with the amount of GLDH added. The coupled catalytic reaction is directly observable by cyclic voltammetry because it is sufficiently fast to regenerate the initial state of the cofactor within the diffusion layer.

Figure 15C:
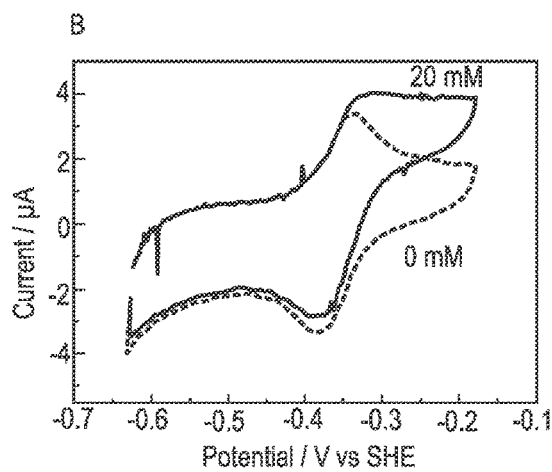
FIG. 15C is a series of cyclic voltammograms of an electrode of the invention vs a standard hydrogen electrode (SHE) for the reverse reaction of FIG. 15B.

FIG. 15C shows the same reaction operated in reverse, where an electrode formed in accordance with Example 1a (geometric area 1.5 cm$^2$) is used for regenerating NADP+, which is then used to oxidize L-glutamate to 2-oxoglutarate with release of NH4+. To observe the voltammetric response in this less favourable direction, it was necessary to co-immobilize GLDH directly onto the larger electrode and use a slower scan rate (1 mV s$^{-1}$). From the beginning, FNR (6 µL of 200 µM) and GLDH (8 µL of 200 µM) were loaded at the same time onto the electrode and incubated for 10 minutes at room temperature before recording the cyclic voltammetry of NADPH (50 µM). Upon injecting L-glutamate (final concentration 20 mM), the oxidation peak converted to a more sigmoidal shape, showing that NADPH is no longer depleted at the electrode surface, and confirming that the electrode also behaves as a NADP+ regeneration system.

Figure 15D:
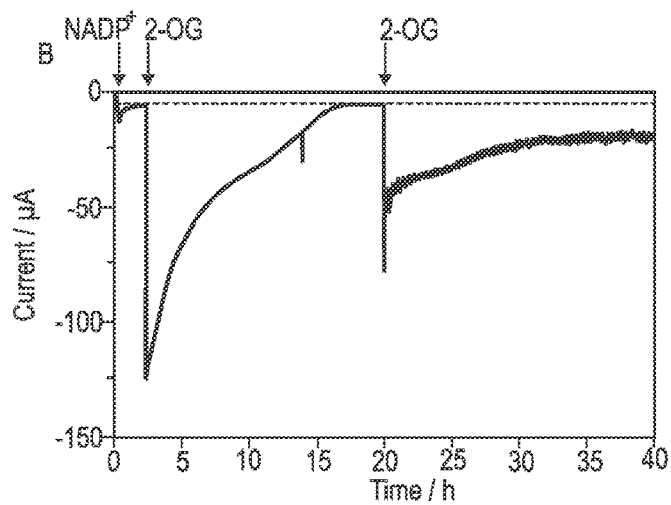
FIG. 15D is a graph showing additions of 2-oxoglutarate when in the presence of an electrode of the invention.

The GLDH-catalysed production of L-glutamate provided an excellent reporting tool for probing cofactor regeneration dynamics. Small-scale bulk conversion experiments were therefore conducted to obtain L-glutamate product for direct detection via NMR analysis, along with simultaneous monitoring of the faradaic charge passed. All experiments were carried out 'on the bench' with the solution agitated by bubbling Ar without any further steps being taken to improve anaerobicity. In all cases, the Pt counter electrode was separated in a side arm linked to the main compartment by a glass frit. In FIG. 15D, an electrode of the invention was used (Example 1a, area 3 cm$^2$) and the experiment was initiated with only GLDH (4 µM) and NH4+ (20 mM) in solution, with the potential held at −0.46 V vs SHE (i.e. 110 mV of overpotential for NADP+ reduction at pH 8.0). Upon injection of NADP+ (20 µM) a reduction current was observed, which decreased exponentially to a steady level after 1.5 h, indicating exhaustive consumption of NADP+ (see below). At this point, 2-oxoglutarate was injected to give a final concentration of 5 mM, which immediately generated a large current that was monitored until it dropped to a similar low background level. After 20 h, an aliquot of the cell solution was removed for NMR analysis. The charge consumed was also determined (FIG. 15E) taking into account the small residual background current that was observed in all chronoamperometric experiments. We attribute the background current to traces of dissolved O2 entering the cell from the atmosphere or through the glass frit, despite continuous bubbling with Ar.

For FIG. 15D, the amount of charge passed before adding 2-oxoglutarate was 8.9 mC, equivalent to 4.6×10$^{-8}$ moles of NADPH (concentration 22 mM, in 2.1 mL of solution). The charge passed after adding 2-oxoglutarate, corrected for background, was 2.01 C, equivalent to 1.04×10$^{-5}$ moles of L-glutamate, giving a concentration of 4.97 mM in 2.1 mL of solution. From NMR, the L-glutamate concentration after 20 h was 5.2 mM, the increase above the expected concentration (5.0 mM) indicating that some concentration had occurred. Based on the coulometric data, the TTN was 226: this compares with 261 using the expected quantity of NADP and the NMR-derived L-glutamate concentration. Errors in coulometric calculations arise from the uncertainty in subtracting background current, whereas errors in chemical quantities arise from the difficulty in accurately weighing small amounts of nicotinamide cofactor and reduction of solution volume over the course of the experiment.

Figure 15E:
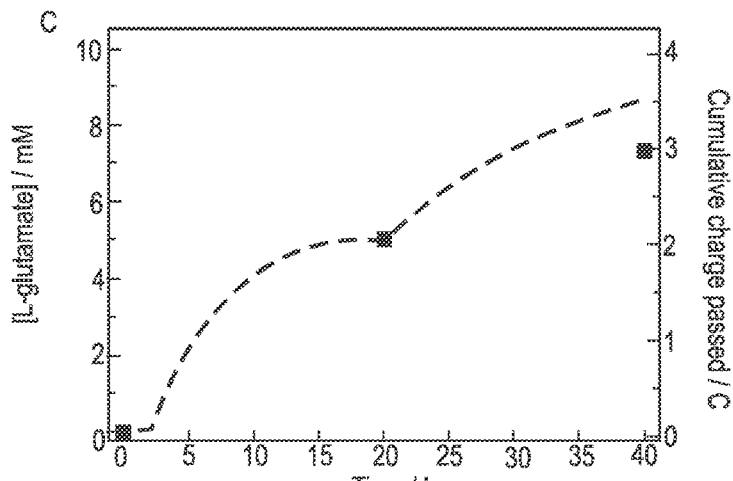
FIG. 15E shows a background subtracted result of the experiment shown in FIG. 15D.

At 20 h, a further addition of 2-oxoglutarate was made, sufficient to give approximately 5 mM final concentration, and the experiment was resumed. The immediate recovery of at least 50% of the expected reduction current showed that the electrode was still active. FIG. 15E includes the product and charge accumulation from this second stage. From an NMR analysis, the L-glutamate concentration after 40 h was 7.31 mM, amounting to 73% conversion (of 10 mM 2-oxoglutarate) and a TTN of 366. After this extended period, when the system is still running, the FNR molecules closest to the ITO surface must have cycled approximately 106 times.

A similar experiment and outcome was achieved using an electrode constructed with flexible Ti foil as support (Example 1d).

Example 9B—In Situ Organic Synthesis

A system, in accordance with the invention, was set up, as shown in FIG. 12, with an electrochemical cell located within a reaction vessel V. The electrochemical cell comprised an electrode 2 of the invention formed in accordance with Example 1c (PGE, area 0.3 cm$^2$).

Figure 16A:
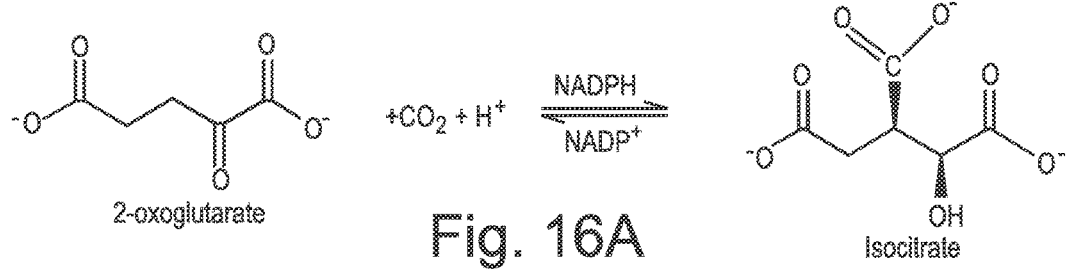
FIG. 16A shows a second reaction scheme of 2-oxoglutarate.

This experiment was arranged to investigate the oxidative decarboxylation of L-isocitrate (see FIG. 16A) catalyzed by isocitrate dehydrogenase (ICDH).

Figure 16B:
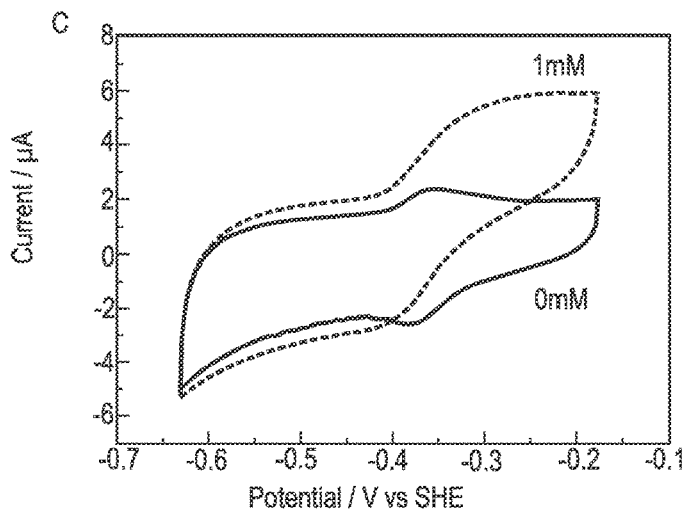
FIG. 16B is a series of cyclic voltammograms showing the oxidative decarboxylation of the reaction of FIG. 16A.

With the electrode in place and the reactants (NADPH 5 µM, Mg$^{2+}$ 2 mM) in the cell a voltammogram was recorded before initiating the coupled reaction by injecting isocitrate (final concentration 1 mM) (see FIG. 16B). The lower NADPH concentration resulted in a clear enhancement of the oxidation current.

Example 9C—In Situ Organic Synthesis

A system in accordance with the invention, was set up, as shown in FIG. 12, with an electrochemical cell located within a reaction vessel V. The electrochemical cell comprised an electrode 2 of the invention formed for runs A, B, D in accordance with Example 1 d (Ti foil 0.127 mm thick with 0.25 mm wire) and for run C a spool of titanium wire (0.25 mm thick) wrapped around a core of titanium wire (0.81 mm thick) to investigate the reaction shown in FIG. 15A. For run C the electrode was left in a solution of FNR for 1 hour with stirring.

Date relevant to the various reaction runs are as set out in Table 1 below:

TABLE 1

Data for four experiment runs of Example 9C

| Electrode | Mols FNR | Average Coverage | Duration | L-glutamate | | TOF* | TTN‡ By charge | TTN‡ By NMR | Rate |
|---|---|---|---|---|---|---|---|---|---|
| Area (cm$^2$) | (nmols) | (pmolcm$^{-2}$) | (h) | mM | μmoles | TON† (s$^{-1}$) | | | (μmoles h$^{-1}$ cm$^{-2}$) |
| A | 17 | 2.3 | 115 | 16.4 | 17.5 | 43.7 | 19356 | 0.33 | 908 | 873 | 0.16 |
| B | 20 | 1.2 | 60 | 19.6 | 20.1 | 50.2 | 41181 | 0.58 | 1137 | 1004 | 0.13 |
| C | 6 | 0.8 | 136 | 37.8 | 20.5 | 51.2 | 62682 | 0.46 | 1108 | 1025 | 0.22 |
| D‡ | 10 | 0.9 | 90 | 41.7 | 13.3 | 33.4 | 37265 | 0.25 | 813 | 667 | 0.08 |

Electrode Area: this is the total area of the electrode.
TTN: Total Turnover number defined as number mols of L-glutamate made per initial number mols of NADP$^+$; mols L-glutamate estimated from charge passed in chronoamperometry and also as measured by NMR.
TON: Turnover Number defined as mols L-glutamate/mols FNR; mols of L-glutamate measured by NMR, mols of FNR calculated from non-turnover peaks measured by cyclic voltammetry.
TOF: Turnover Frequency defined as mols L-glutamate/mols FNR/second
In each of runs A to C the experimental conditions were as follows:
Electrode potential held at −0.46 V vs SHE; 50 mM borate, pH 8; 20 μM NADP$^+$; 40 mM NH$_4^+$; 30 mM 2-oxoglutarate; 3.2 μM glutamate dehydrogenase; 20° C.; Argon bubbled into cell throughout run
In run D the experimental conditions were as follows:
Electrode potential held at −0.46 V vs SHE; 50 mM borate, pH 8; 20 μM NADP$^+$; 40 mM NH$_4^+$; 20 mM 2-oxoglutarate; 3.2 μM glutamate dehydrogenase; 20° C.; no Argon bubbled into cell up to 22 hours (diffusion limited), Argon bubbling from 22 hours onwards Electrode Area: this is the total area of the electrode.

TTN: Total Turnover number defined as number mols of L-glutamate made per initial number mols of NADP$^+$; mols L-glutamate estimated from charge passed in chronoamperometry and also as measured by NMR.

TON: Turnover Number defined as mols L-glutamate/mols FNR; mols of L-glutamate measured by NMR, mols of FNR calculated from non-turnover peaks measured by cyclic voltammetry.

TOF: Turnover Frequency defined as mols L-glutamate/mols FNR/second

In each of runs A to C the experimental conditions were as follows:

Electrode potential held at −0.46 V vs SHE; 50 mM borate, pH 8; 20 μM NADP$^+$; 40 mM NH$_4^+$; 30 mM 2-oxoglutarate; 3.2 μM glutamate dehydrogenase; 20° C.; Argon bubbled into cell throughout run In run D the experimental conditions were as follows:

Electrode potential held at −0.46 V vs SHE; 50 mM borate, pH 8; 20 μM NADP$^+$; 40 mM NH$_4^+$; 20 mM 2-oxoglutarate; 3.2 μM glutamate dehydrogenase; 20° C.; no Argon bubbled into cell up to 22 hours (diffusion limited), Argon bubbling from 22 hours onwards The above data, show improved turnover numbers and total turnover numbers as compared to earlier experiments. Without wishing or intended to be bound by any particular theory we believe that this is due to improved packing of the electrodes within the cell and an increase in the surface area to volume ratio of the electrode within the cell. By reducing and/or controlling the pathway the diffusion limitation of any reactions can be achieved.

The electrode of the invention can be utilized as a module component for near universal deployment or may be made bespoke depending upon the desired use. As will be appreciated the electrode of the invention is simple to use, requires no other enzymes for cofactor regeneration and no other chemicals are required.

Indeed, the electrode of the invention is formable in a cell with a second electrode and a DC power supply to provide an electrochemical regenerating system capable of driving industrially-relevant chemical reactions.

As will be appreciated, the electrode of the invention can be embodied in transparent media (for example ITO and/or FTO on glass substrates). This opens the possibility of using light to drive the reaction, and hence useful chemical reactions.

Figure 17A:
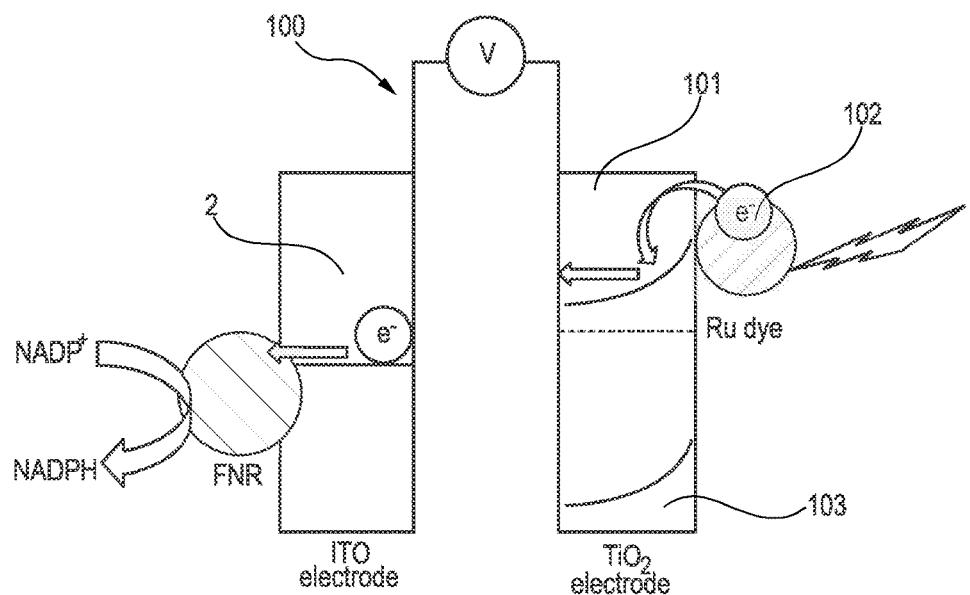
FIG. 17A shows a cell of the invention.

FIG. 17A shows a photoactive system 100 comprising an electrode of the invention 2 and a photocathode 101, in this case comprising a dye 102 and TiO$^2$ electrode 103. As will be appreciated, as the light is turned on, the effect will be to drive cycling of the NADP+/NADPH couple.

Example 10—Light Driven NADPH Recycling

The cell 101 of FIG. 17A was deployed to demonstrate reaction of NADP+.

A solution was prepared of MES buffer (0.2M, pH 7, 20° C.) and the electrode 1 inserted therein. The system was illuminated by a projector lamp (λ>420 nm).

Figure 17B:
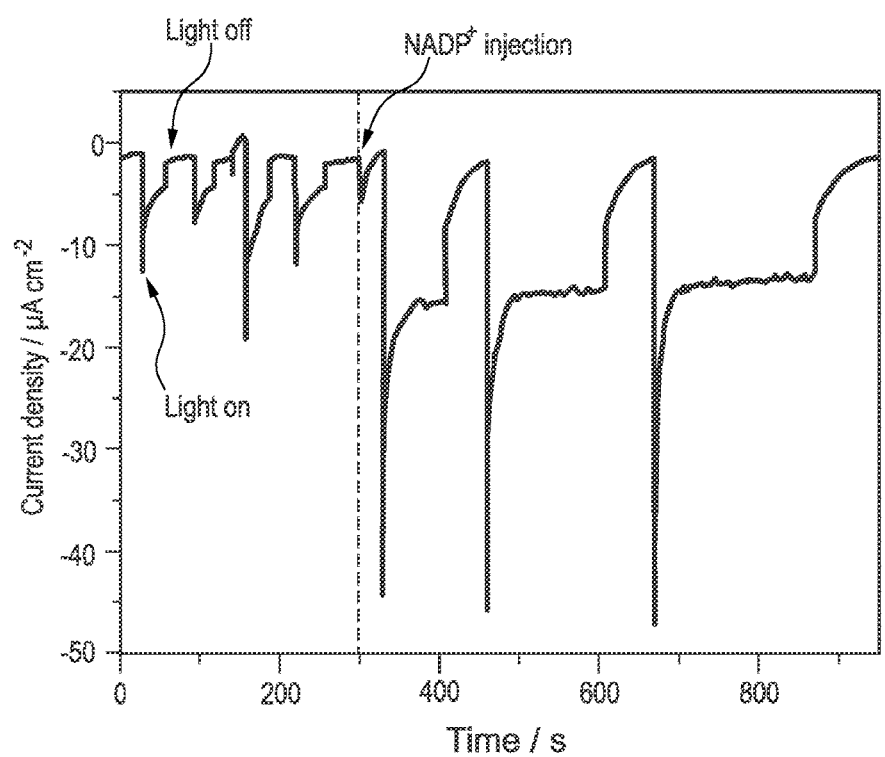
FIG. 17B shows experimental data relating to the use of the cell of FIG. 17A.

Referring to FIG. 17B, in the left hand zone of the graph the solution is absent NADP+ and the light is turned on and off to demonstrate responsiveness.

The dotted line indicates the time of NADP+ injection (0.38 mM), clearly demonstrating activity.

The cell 100 could therefore be deployed without the need for a dedicated power source but could instead harvest light to drive organic synthesis.

As will be appreciated we have demonstrated the activity of a simple FNR electrode which is capable of driving organic synthesis simply and effectively, whether powered by a DC power source or light.

Although the above Examples and exemplification has discussed the recycling of NADPH, the current invention is equally applicable to the NAD+/NADH couple. As will be appreciated, the only difference between NADP+ (FIG. 2B) and NAD+ is the presence of the phosphate group of NADP$^+$. Whilst the difference between NAD+ and NADP+ appears minor, there is a significant difference in each cofactor's ability to bind to FNR (with NADP+ being about 500 times stronger). That said, by carefully controlling concentrations (and other optimization strategies suggested above) it is possible to deploy the invention to drive the NAD+/NADH cycle.

The invention claimed is:

1. An electrochemical cell comprising an electrode, the electrode comprising a substrate on which is located a porous layer of a conducting oxide and having located thereon Ferredoxin NADP Reductase (FNR), wherein the conducting oxide of the porous layer is not a semi-conducting oxide and is not selected from one or more of SrTiO$_3$, TiO$_2$, doped TiO$_2$ or doped ZrO$_2$.

2. An electrochemical cell comprising an electrode according to claim 1, wherein the porous layer of a conducting oxide has a thickness of over 0.1, 0.2, 0.3, 0.4 or 0.5 μm.

3. An electrochemical cell comprising an electrode according to claim 1, wherein the porous layer of a conducting oxide has a thickness of from 0.5 to 500 μm.

4. An electrochemical cell comprising an electrode according to claim 1, wherein the porous layer of a conducting oxide has pore sizes in the range of 50 to 1000 nm.

5. An electrochemical cell comprising an electrode according to claim 1, wherein the porous layer of a conducting oxide is formed from nanoparticles.

6. An electrochemical cell comprising an electrode according to claim 1, wherein the porous layer of a conducting oxide is formed from particles having an average diameter in the range of 10 to 1000 nm.

7. An electrochemical cell comprising an electrode according to claim 1, wherein the conducting oxide of the porous layer of a conducting oxide is selected from one or more of indium tin oxide (ITO) or fluorine doped tin oxide (FTO).

8. An electrochemical cell comprising an electrode according to claim 1, wherein the substrate comprises or is an electrically conductive layer.

9. An electrochemical cell comprising an electrode according to claim 8, wherein the electrically conductive layer is selected from indium tin oxide (ITO), fluorine doped tin oxide (FTO), metal, carbon, aluminum-doped zinc oxide (AZO) or indium-doped cadmium oxide (ICO).

10. An electrochemical cell comprising an electrode according to claim 8, wherein the electrically conductive layer is optically transparent or is substantially optically transparent.

11. An electrochemical cell comprising an electrode according to claim 8, wherein the electrically conductive layer has a metal wire provided thereon.

12. An electrochemical cell comprising an electrode according to claim 1, wherein the substrate comprises an inert support layer.

13. An electrochemical cell comprising an electrode according to claim 12, wherein the inert support layer is selected from a glass or a polymeric material.

14. An electrochemical cell comprising an electrode according claim 1, wherein one or more further enzymes is or are immobilized on the electrode.

15. An electrochemical cell comprising an electrode according to claim 1, wherein the porous layer of a conducting oxide has pore sizes in the range of 60 to 1000 nm.

16. An electrochemical cell according to claim 1, wherein the substrate is non-optically transparent.

17. An electrochemical cell according to claim 16, wherein the substrate is formed from carbon or metal.

18. An electrochemical cell according to claim 1, wherein the substrate is formed, at least in part, from carbon or metal.

19. An electrochemical cell comprising an electrode, the electrode comprising a substrate on which is located a porous layer of a conducting oxide and having located thereon Ferredoxin NADP Reductase (FNR), wherein the conducting oxide of the porous layer of a conducting oxide comprises one or more of indium tin oxide (ITO) or fluorine doped tin oxide (FTO).

* * * * *